(12) United States Patent
Itagaki et al.

(10) Patent No.: US 7,709,651 B2
(45) Date of Patent: May 4, 2010

(54) PROCESS FOR PRODUCING OPTICALLY ACTIVE CYCLOPROPANE COMPOUND AND ASYMMETRIC COPPER COMPLEX FOR USE IN THE SAME

(75) Inventors: Makoto Itagaki, Katano (JP); Katsuhisa Masumoto, Ibaraki (JP); Ryo Minamida, Kyotanabe (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 1017 days.

(21) Appl. No.: 10/572,391

(22) PCT Filed: Sep. 17, 2004

(86) PCT No.: PCT/JP2004/014031

§ 371 (c)(1),
(2), (4) Date: Mar. 16, 2006

(87) PCT Pub. No.: WO2005/028413

PCT Pub. Date: Mar. 31, 2005

(65) Prior Publication Data

US 2007/0032659 A1    Feb. 8, 2007

(30) Foreign Application Priority Data

Sep. 19, 2003    (JP)  .............................. 2003-327712

(51) Int. Cl.
*C07F 1/08* (2006.01)
*C07C 69/74* (2006.01)
(52) U.S. Cl. ...................................... 548/101; 560/124
(58) Field of Classification Search ................... 548/101
See application file for complete search history.

(56) References Cited

U.S. PATENT DOCUMENTS

| 6,072,081 A | 6/2000 | Itagaki et al. |
| 6,410,741 B1 | 6/2002 | Itagaki et al. |
| 6,858,559 B2 | 2/2005 | Yamamoto et al. |

FOREIGN PATENT DOCUMENTS

| EP | 0895992 A2 | 2/1999 |
| JP | 2003-12675 A | 1/2003 |

OTHER PUBLICATIONS

Charette et al., Tetrahedron: Asymmetry, vol. 14, pp. 867-872, (2003).
Deeth et al., Organometallics, vol. 23, No. 5, pp. 1042-1054, (2004).
Denmark et al., J. Org. Chem., vol. 65, No. 18, pp. 5875 to 5878, (2000).
Lowenthal et al., Tetrahedron Letters, vol. 32, No. 50, pp. 7373-7376, (1991).
Østergaard et al., Tetrahedron, vol. 57, pp. 6083-6088, (2001).
Andre B. Charette et al., 'Bis (oxazoline)-copper (1)-catalyzed enantioselective cyclopropanation of cinnamate esters with diazomethane', Tetrahedron: Asymmetry, 2003, No. 14, pp. 867-872.
Robert J. Deeth et al., 'AMolecular Mechanics Study of Copper (II)-Cathlyzed Asymmetric Diels-Alder Reactions', Organometallics, 2004, vol. 23, No. 5, pp. 1042-1054.
Scott E. Denmark et al., 'Effect of Ligand Structure in the Bisoxazoline Mediated Asymmetric Addition of Methyllithium to Imines', 2000, vol. 65, No. 18, pp. 5875 to 5878.
Alexander et al., Tetrahedron Letters, vol. 41, pp. 7135-7138, (2000).

*Primary Examiner*—Kamal A Saeed
(74) *Attorney, Agent, or Firm*—Birch, Stewart, Kolasch & Birch, LLP

(57) ABSTRACT

A process for producing an optically active cyclopropane compound represented by the formula (4):

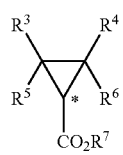

(4)

wherein $R^3$, $R^4$, $R^5$ and $R^6$ are the same or different, and represent a hydrogen atom, a halogen atom, a substituted or unsubstituted alkyl group, and so on; and $R^7$ represents a C1-6 alkyl group; and * represents an asymmetric carbon atom, which comprises reacting a prochiral olefin represented by the formula (2):

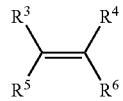

(2)

wherein $R^3$, $R^4$, $R^5$, and $R^6$ are as described above,
with a diazoacetic acid ester represented by the formula (3):

$$N_2CHCO_2R^7 \qquad (3)$$

wherein $R^7$ is as defined above,
in the presence of an asymmetric copper complex prepared from an optically active cycloalkylidenebisoxazoline compound represented by the formula (1):

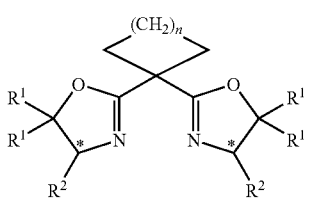

(1)

wherein $R^1$ represents a hydrogen atom, a C1-6 alkyl group, and so on; $R^2$ represents a C1-6 alkyl group and so on; and n represents an integer of 0 to 3; provided that, two $R^1$s may be bonded each other together with the carbon atom to which they are bonded to form a ring; and * represents an asymmetric carbon atom,
and a copper compound, is provided.

8 Claims, No Drawings

PROCESS FOR PRODUCING OPTICALLY ACTIVE CYCLOPROPANE COMPOUND AND ASYMMETRIC COPPER COMPLEX FOR USE IN THE SAME

TECHNICAL FIELD

The present invention relates to a process for producing an optically active cyclopropane compound and an asymmetric copper complex for use in the same.

BACKGROUND ART

Optically active cyclopropane compounds whose representative examples are (+)-trans-2,2-dimethyl-3-(2-methyl-1-propenyl)cyclopropanecarboxylic acid ester and (+)-trans-3,3-dimethyl-2-(benzyloxymethyl)cyclopropanecarboxylic acid ester are important compounds as synthetic intermediates of pesticides and pharmaceuticals such as synthesized pyrethroid insecticides. As the process for producing the optically active cyclopropane compound, methods for carrying out asymmetric cyclopropanation of a prochiral olefin using an asymmetric copper complex prepared from an optically active bisoxazoline compound and a copper compound as a catalyst have been known (e.g. JP 11-171874 A, Tetrahedron Lett., 32, 7373 (1991) and Tetrahedron, 57, 6083 (2001)). However, these methods were not always enough for the selectivity of (+)-trans-isomer of the desirable cyclopropane compound when a diazoacetic acid lower alkyl ester such as ethyl diazoacetate was used, and it was needed to use a particular diazoacetic acid ester such as diazoacetic acid (2,6-di-tert-butyl-4-methylphenyl) ester to improve the selectivity.

DISCLOSURE OF THE INVENTION

According to the process of the present invention, an optically active trans cyclopropane compound can be obtained efficiently from a diazoacetic acid lower alkyl ester which is an industrially advantageous and a prochiral olefin by using a novel asymmetric copper complex prepared from the optically active cycloalkylidenebisoxazoline compound represented by the formula (1) described below and a copper compound.

That is, the present invention provides a process for producing an optically active cyclopropane compound represented by the formula (4):

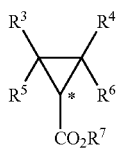

(4)

wherein $R^3$, $R^4$, $R^5$ and $R^6$ are the same or different, and represent a hydrogen atom, a halogen atom, a substituted or unsubstituted alkyl group,
a substituted or unsubstituted alkenyl group, a substituted or unsubstituted aryl group,
a substituted or unsubstituted aralkyl group or
a substituted or unsubstituted alkoxycarbonyl group;
provided that, when $R^3$ and $R^5$ are the same, $R^4$ and $R^6$ are different from each other; and
$R^7$ represents an alkyl group having 1 to 6 carbon atoms, which comprises reacting a prochiral olefin represented by the formula (2):

wherein $R^3$, $R^4$, $R^5$, and $R^6$ are as described above, with a diazoacetic acid ester represented by the formula (3):

$$N_2CHCO_2R^7 \qquad (3)$$

wherein $R^7$ is as defined above,
in the presence of an asymmetric copper complex prepared from an optically active cycloalkylidenebisoxazoline compound represented by the formula (1):

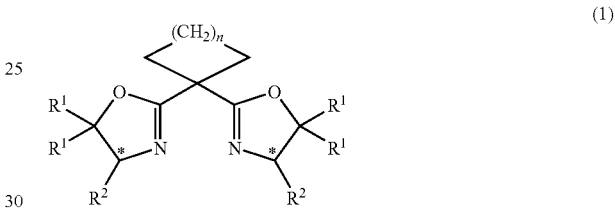

(1)

wherein $R^1$ represents a hydrogen atom, a C1-6 alkyl group, a substituted or unsubstituted aralkyl group or a substituted or unsubstituted phenyl group,
$R^2$ represents a C1-6 alkyl group, a substituted or unsubstituted aralkyl group or a substituted or unsubstituted phenyl group, and n represents an integer of 0 to 3;
provided that, when $R^1$ represents a C1-6 alkyl group, two $R^1$'s which are bonded to the same carbon atom may be bonded together with the carbon atom to which they are bonded to form a ring; and * represents an asymmetric carbon atom; and a copper compound.

BEST MODE FOR CARRYING OUT THE PRESENT INVENTION

First, the asymmetric copper complex prepared from the optically active cycloalkylidenebisoxazoline compound represented by the formula (1) (hereinafter, simply referred to as the optically active bisoxazoline compound (1)) and the copper compound will be illustrated.

In the optically active bisoxazoline compound (1), examples of the alkyl groups having 1 to 6 carbon atoms represented by $R^1$ or $R^2$ include straight or branched chain alkyl groups such as a methyl, ethyl, n-propyl, isopropyl, n-butyl, isobutyl, n-pentyl, and n-hexyl group.

As the unsubstituted aralkyl groups represented by $R^1$ or $R^2$, C7-16 aralkyl groups which are C1-6 alkyl groups substituted with a aryl group such as a phenyl and naphthyl group are exemplified. As the substituents of the substituted aralkyl groups, at least one group selected from alkyl groups and alkoxy groups is exemplified. Examples of the alkyl groups and the alkoxy groups include C1-6 alkyl groups and C1-6 alkoxy groups respectively. Specific examples thereof include a benzyl, 2-methylbenzyl, 3-methylbenzyl, 4-methylbenzyl, 2-methoxybenzyl, 3-methoxybenzyl, 4-methoxybenzyl, 1-naphthylmethyl, and 2-naphthylmethyl group.

As the substituents of the substituted phenyl groups represented by $R^1$ or $R^2$, at least one group selected from alkyl groups and alkoxy groups is exemplified. Examples of the alkyl groups and the alkoxy groups include C1-6 alkyl groups and C1-6 alkoxy groups respectively. Specific examples thereof include a 4-methylphenyl and 3-methoxyphenyl group.

As the substituted or unsubstituted aralkyl groups represented by $R^1$, C7-16 aralkyl groups which may be substituted with at least one substituent selected from C1-6 alkyl groups and C1-6 alkoxy groups are exemplified. Examples of the substituted or unsubstituted phenyl groups include phenyl groups which may be substituted with at least one substituent selected from C1-6 alkyl groups and C1-6 alkoxy groups.

As the substituted or unsubstituted aralkyl groups represented by $R^2$, C7-16 aralkyl groups which may be substituted with at least one substituent selected from C1-6 alkyl groups and C1-6 alkoxy groups are exemplified. Examples of the substituted or unsubstituted phenyl groups include phenyl groups which may be substituted with at least one substituent selected from the C1-6 alkyl groups and the C1-6 alkoxy groups. $R^2$ is preferably a t-butyl group.

Examples of the C1-6 alkyl of the C1-6 alkyl groups and the C1-6 alkoxy groups which are substituents of the substituted aralkyl groups or the substituted phenyl groups described above include straight chain or branched chain alkyl groups such as a methyl, ethyl, n-propyl, isopropyl, n-butyl, isobutyl, n-pentyl, and n-hexyl group like the above.

When two $R^1$s represent C1-6 alkyl groups, as the ring formed by bonding two $R^1$s which are bonded to the same carbon atom together with the carbon atom to which they are bonded, a cyclopropane, cyclobutane, cyclopentane, cyclohexane, and cycloheptane ring are exemplified.

In the formula of the optically active bisoxazoline compound (1), n represents an integer of 0 to 3. For example, when n is 0, it represents a cyclopropylidenebisoxazoline compound.

Examples of the optically active bisoxazoline compound (1) include 1,1-bis[2-[(4S)-methyloxazoline]]cyclopropane, 1,1-bis[2-[(4S)-methyl-5,5-dimethyloxazoline]]cyclopropane, 1,1-bis[2-[(4S)-methyl-5,5-diethyloxazoline]]cyclopropane, 1,1-bis[2-[(4S)-methyl-5,5-di-n-propyloxazoline]]cyclopropane, 1,1-bis[2-[(4S)-methyl-5,5-di-n-butyloxazoline]]cyclopropane, 1,1-bis[2-[(4S)-methyl-5,5-diisobutyloxazoline]]cyclopropane, 1,1-bis[2-[(4S)-methyl-5,5-di-n-pentyloxazoline]]cyclopropane, 1,1-bis[2-[(4S)-methyl-5,5-di-n-hexyloxazoline]]cyclopropane, 1,1-bis[2-[(4S)-methyl-5,5-dibenzyloxazoline]]cyclopropane, 1,1-bis[2-[(4S)-methyl-5,5-di(2-methylbenzyl)oxazoline]]cyclopropane, 1,1-bis[2-[(4S)-methyl-5,5-di(3-methylbenzyl)oxazoline]]cyclopropane, 1,1-bis[2-[(4S)-methyl-5,5-di(4-methylbenzyl)oxazoline]]cyclopropane, 1,1-bis[2-[(4S)-methyl-5,5-di(2-methoxybenzyl)oxazoline]]cyclopropane, 1,1-bis[2-[(4S)-methyl-5,5-di(3-methoxybenzyl)oxazoline]]cyclopropane, 1,1-bis[2-[(4S)-methyl-5,5-di(4-methoxybenzyl)oxazoline]]cyclopropane,
1,1-bis[2-[(4S)-methyl-5,5-di(1-naphthylmethyl)oxazoline]]cyclopropane, 1,1-bis[2-[(4S)-methyl-5,5-di(2-naphthylmethyl)oxazoline]]cyclopropane, 1,1-bis[2-[(4S)-methyl-5,5-diphenyloxazoline]]cyclopropane, 1,1-bis[2-[(4S)-methyl-5,5-di(3-methylphenyl)oxazoline]]cyclopropane, 1,1-bis[2-[(4S)-methyl-5,5-di(4-methylphenyl)oxazoline]]cyclopropane, 1,1-bis[2-[(4S)-methyl-5,5-di(2-methoxyphenyl)oxazoline]]cyclopropane, 1,1-bis[2-[(4S)-methyl-5,5-di(3-methoxyphenyl)oxazoline]]cyclopropane, 1,1-bis[2-[(4S)-methyl-5,5-di(4-methoxyphenyl)oxazoline]]cyclopropane, 1,1-bis[2-[spiro[(4S)-methyloxazoline-5,1'-cyclopropane]]]cyclopropane, 1,1-bis[2-[spiro[(4S)-methyloxazoline-5,1'-cyclopentane]]]cyclopropane, 1,1-bis[2-[spiro[(4S)-methyloxazoline-5,1'-cycloheptane]]]cyclopropane,
1,1-bis[2-[(4S)-isopropyloxazoline]]cyclopropane, 1,1-bis[2-[(4S)-isopropyl-5,5-dimethyloxazoline]]cyclopropane, 1,1-bis[2-[(4S)-isopropyl-5,5-diethyloxazoline]]cyclopropane,
1,1-bis[2-[(4S)-isopropyl-5,5-di-n-propyloxazoline]]cyclopropane, 1,1-bis[2-[(4S)-isopropyl-5,5-di-n-butyloxazoline]]cyclopropane, 1,1-bis[2-[(4S)-isopropyl-5,5-diisobutyloxazoline]]cyclopropane, 1,1-bis[2-[(4S)-isopropyl-5,5-di-n-pentyloxazoline]]cyclopropane, 1,1-bis[2-[(4S)-isopropyl-5,5-di-n-hexyloxazoline]]cyclopropane, 1,1-bis[2-[(4S)-isopropyl-5,5-dibenzyloxazoline]]cyclopropane, 1,1-bis[2-[(4S)-isopropyl-5,5-di(2-methylbenzyl)oxazoline]]cyclopropane, 1,1-bis[2-[(4S)-isopropyl-5,5-di(3-methylbenzyl)oxazoline]]cyclopropane, 1,1-bis[2-[(4S)-isopropyl-5,5-di(4-methylbenzyl)oxazoline]]cyclopropane, 1,1-bis[2-[(4S)-isopropyl-5,5-di(2-methoxybenzyl)oxazoline]]cyclopropane, 1,1-bis[2-[(4S)-isopropyl-5,5-di(3-methoxybenzyl)oxazoline]]cyclopropane,
1,1-bis[2-[(4S)-isopropyl-5,5-di(4-methoxybenzyl)oxazoline]]cyclopropane, 1,1-bis[2-[(4S)-isopropyl-5,5-di(1-naphthylmethyl)oxazoline]]cyclopropane, 1,1-bis[2-[(4S)-isopropyl-5,5-di(2-naphthylmethyl)oxazoline]]cyclopropane, 1,1-bis[2-[(4S)-isopropyl-5,5-diphenyloxazoline]]cyclopropane, 1,1-bis[2-[(4S)-isopropyl-5,5-di(3-methylphenyl)oxazoline]]cyclopropane, 1,1-bis[2-[(4S)-isopropyl-5,5-di(4-methylphenyl)oxazoline]]cyclopropane, 1,1-bis[2-[(4S)-isopropyl-5,5-di(2-methoxyphenyl)oxazoline]]cyclopropane, 1,1-bis[2-[(4S)-isopropyl-5,5-di(3-methoxyphenyl)oxazoline]]cyclopropane, 1,1-bis[2-[(4S)-isopropyl-5,5-di(4-methoxyphenyl)oxazoline]]cyclopropane, 1,1-bis[2-[spiro[(4S)-isopropyloxazoline-5,1'-cyclopropane]]]cyclopropane, 1,1-bis[2-[spiro[(4S)-isopropyloxazoline-5,1'-cyclopentane]]]cyclopropane, 1,1-bis[2-[spiro[(4S)-isopropyloxazoline-5,1'-cycloheptane]]]cyclopropane,
1,1-bis[2-[(4S)-isobutyloxazoline]]cyclopropane, 1,1-bis[2-[(4S)-isobutyl-5,5-dimethyloxazoline]]cyclopropane, 1,1-bis[2-[(4S)-isobutyl-5,5-diethyloxazoline]]cyclopropane, 1,1-bis[2-[(4S)-isobutyl-5,5-di-n-propyloxazoline]]cyclopropane, 1,1-bis[2-[(4S)-isobutyl-5,5-di-n-butyloxazoline]]cyclopropane, 1,1-bis[2-[(4S)-isobutyl-5,5-diisobutyloxazoline]]cyclopropane, 1,1-bis[2-[(4S)-isobutyl-5,5-di-n-pentyloxazoline]]cyclopropane, 1,1-bis[2-[(4S)-isobutyl-5,5-di-n-hexyloxazoline]]cyclopropane, 1,1-bis[2-[(4S)-isobutyl-5,5-dibenzyloxazoline]]cyclopropane, 1,1-bis[2-[(4S)-isobutyl-5,5-di(2-methylbenzyl)oxazoline]]cyclopropane, 1,1-bis[2-[(4S)-isobutyl-5,5-di(3-methylbenzyl)oxazoline]]cyclopropane, 1,1-bis[2-[(4S)-isobutyl-5,5-di(4-methylbenzyl)oxazoline]]cyclopropane, 1,1-bis[2-[(4S)-isobutyl-5,5-di(2-methoxybenzyl)oxazoline]]cyclopropane, 1,1-bis[2-[(4S)-isobutyl-5,5-di(3-methoxybenzyl)oxazoline]]cyclopropane, 1,1-bis[2-[(4S)-isobutyl-5,5-di(4-methoxybenzyl)oxazoline]]cyclopropane,
1,1-bis[2-[(4S)-isobutyl-5,5-di(1-naphthylmethyl)oxazoline]]cyclopropane, 1,1-bis[2-[(4S)-isobutyl-5,5-di(2-naphthylmethyl)oxazoline]]cyclopropane, 1,1-bis[2-

[(4S)-isobutyl-5,5-diphenyloxazoline]]cyclopropane, 1,1-bis[2-[(4S)-isobutyl-5,5-di(3-methylphenyl)oxazoline]]cyclopropane, 1,1-bis[2-[(4S)-isobutyl-5,5-di(4-methylphenyl)oxazoline]]cyclopropane, 1,1-bis[2-[(4S)-isobutyl-5,5-di(2-methoxyphenyl)oxazoline]]cyclopropane, 1,1-bis[2-[(4S)-isobutyl-5,5-di(3-methoxyphenyl)oxazoline]]cyclopropane, 1,1-bis[2-[(4S)-isobutyl-5,5-di(4-methoxyphenyl)oxazoline]]cyclopropane, 1,1-bis[2-[spiro[(4S)-isobutyloxazoline-5,1'-cyclopropane]]]cyclopropane, 1,1-bis[2-[spiro[(4S)-isobutyloxazoline-5,1'-cyclopentane]]]cyclopropane, 1,1-bis[2-[spiro[(4S)-isobutyloxazoline-5,1'-cycloheptane]]]cyclopropane, 1,1-bis[2-[(4S)-tert-butyloxazoline]]cyclopropane, 1,1-bis[2-[(4S)-tert-butyl-5,5-dimethyloxazoline]]cyclopropane, 1,1-bis[2-[(4S)-tert-butyl-5,5-diethyloxazoline]]cyclopropane, 1,1-bis[2-[(4S)-tert-butyl-5,5-di-n-propyloxazoline]]cyclopropane, 1,1-bis[2-[(4S)-tert-butyl-5,5-di-n-butyloxazoline]]cyclopropane, 1,1-bis[2-[(4S)-tert-butyl-5,5-diisobutyloxazoline]]cyclopropane, 1,1-bis[2-[(4S)-tert-butyl-5,5-di-n-pentyloxazoline]]cyclopropane, 1,1-bis[2-[(4S)-tert-butyl-5,5-di-n-hexyloxazoline]]cyclopropane, 1,1-bis[2-[(4S)-tert-butyl-5,5-dibenzyloxazoline]]cyclopropane, 1,1-bis[2-[(4S)-tert-butyl-5,5-di(2-methylbenzyl)oxazoline]]cyclopropane, 1,1-bis[2-[(4S)-tert-butyl-5,5-di(3-methylbenzyl)oxazolinel]]cyclopropane, 1,1-bis[2-[(4S)-tert-butyl-5,5-di(4-methylbenzyl)oxazoline]]cyclopropane, 1,1-bis[2-[(4S)-tert-butyl-5,5-di(2-methoxybenzyl)oxazoline]]cyclopropane, 1,1-bis[2-[(4S)-tert-butyl-5,5-di(3-methoxybenzyl)oxazoline]]cyclopropane, 1,1-bis[2-[(4S)-tert-butyl-5,5-di(4-methoxybenzyl)oxazoline]]cyclopropane, 1,1-bis[2-[(4S)-tert-butyl-5,5-di(1-naphthylmethyl)oxazoline]]cyclopropane, 1,1-bis[2-[(4S)-tert-butyl-5,5-di(2-naphthylmethyl)oxazoline]]cyclopropane, 1,1-bis[2-[(4S)-tert-butyl-5,5-diphenyloxazolinel]]cyclopropane, 1,1-bis[2-[(4S)-tert-butyl-5,5-di(3-methylphenyl)oxazoline]]cyclopropane, 1,1-bis[2-[(4S)-tert-butyl-5,5-di(4-methylphenyl)oxazoline]]cyclopropane, 1,1-bis[2-[(4S)-tert-butyl-5,5-di(2-methoxyphenyl)oxazoline]]cyclopropane, 1,1-bis[2-[(4S)-tert-butyl-5,5-di(3-methoxyphenyl)oxazoline]]cyclopropane, 1,1-bis[2-[(4S)-tert-butyl-5,5-di(4-methoxyphenyl)oxazoline]]cyclopropane, 1,1-bis[2-[spiro[(4S)-tert-butyloxazoline-5,1'-cyclopropane]]]cyclopropane, 1,1-bis[2-[spiro[(4S)-tert-butyloxazoline-5,1'-cyclopentane]]]cyclopropane, 1,1-bis[2-[spiro[(4S)-tert-butyloxazoline-5,1'-cycloheptane]]]cyclopropane, 1,1-bis[2-[(4S)-benzyloxazoline]]cyclopropane, 1,1-bis[2-[(4S)-benzyl-5,5-dimethyloxazoline]]cyclopropane, 1,1-bis[2-[(4S)-benzyl-5,5-diethyloxazoline]]cyclopropane, 1,1-bis[2-[(4S)-benzyl-5,5-di-n-propyloxazoline]]cyclopropane, 1,1-bis[2-[(4S)-benzyl-5,5-di-n-butyloxazoline]]cyclopropane, 1,1-bis[2-[(4S)-benzyl-5,5-diisobutyloxazoline]]cyclopropane, 1,1-bis[2-[(4S)-benzyl-5,5-di-n-pentyloxazoline]]cyclopropane, 1,1-bis[2-[(4S)-benzyl-5,5-di-n-hexyloxazoline]]cyclopropane, 1,1-bis[2-[(4S)-benzyl-5,5-dibenzyloxazoline]]cyclopropane, 1,1-bis[2-[(4S)-benzyl-5,5-di(2-methylbenzyl)oxazoline]]cyclopropane, 1,1-bis[2-[(4S)-benzyl-5,5-di(3-methylbenzyl)oxazoline]]cyclopropane, 1,1-bis[2-[(4S)-benzyl-5,5-di(4-methylbenzyl)oxazoline]]cyclopropane, 1,1-bis[2-[(4S)-benzyl-5,5-di(2-methoxybenzyl)oxazoline]]cyclopropane, 1,1-bis[2-[(4S)-benzyl-5,5-di(3-methoxybenzyl)oxazoline]]cyclopropane, 1,1-bis[2-[(4S)-benzyl-5,5-di(4-methoxybenzyl)oxazoline]]cyclopropane, 1,1-bis[2-[(4S)-benzyl-5,5-di(1-naphthylmethyl)oxazoline]]cyclopropane, 1,1-bis[2-[(4S)-benzyl-5,5-di(2-naphthylmethyl)oxazoline]]cyclopropane, 1,1-bis[2-[(4S)-benzyl-5,5-diphenyloxazoline]]cyclopropane, 1,1-bis[2-[(4S)-benzyl-5,5-di(3-methylphenyl)oxazoline]]cyclopropane, 1,1-bis[2-[(4S)-benzyl-5,5-di(4-methylphenyl)oxazoline]]cyclopropane, 1,1-bis[2-[(4S)-benzyl-5,5-di(2-methoxyphenyl)oxazoline]]cyclopropane, 1,1-bis[2-[(4S)-benzyl-5,5-di(3-methoxyphenyl)oxazoline]]cyclopropane, 1,1-bis[2-[(4S)-benzyl-5,5-di(4-methoxyphenyl)oxazoline]]cyclopropane, 1,1-bis[2-[spiro[(4S)-benzyloxazoline-5,1'-cyclopropane]]]cyclopropane, 1,1-bis[2-[spiro[(4S)-benzyloxazoline-5,1'-cyclopentane]]]cyclopropane, 1,1-bis[2-[spiro[(4S)-benzyloxazoline-5,1'-cycloheptane]]]cyclopropane, 1,1-bis[2-[(4S)-phenyloxazoline]]cyclopropane, 1,1-bis[2-[(4S)-phenyl-5,5-dimethyloxazoline]]cyclopropane, 1,1-bis[2-[(4S)-phenyl-5,5-diethyloxazoline]]cyclopropane, 1,1-bis[2-[(4S)-phenyl-5,5-di-n-propyloxazoline]]cyclopropane, 1,1-bis[2-[(4S)-phenyl-5,5-di-n-butyloxazoline]]cyclopropane, 1,1-bis[2-[(4S)-phenyl-5,5-diisobutyloxazoline]]cyclopropane, 1,1-bis[2-[(4S)-phenyl-5,5-di-n-pentyloxazoline]]cyclopropane, 1,1-bis[2-[(4S)-phenyl-5,5-di-n-hexyloxazoline]]cyclopropane, 1,1-bis[2-[(4S)-phenyl-5,5-dibenzyloxazoline]]cyclopropane, 1,1-bis[2-[(4S)-phenyl-5,5-di(2-methylbenzyl)oxazoline]]cyclopropane, 1,1-bis[2-[(4S)-phenyl-5,5-di(3-methylbenzyl)oxazoline]]cyclopropane, 1,1-bis[2-[(4S)-phenyl-5,5-di(4-methylbenzyl)oxazoline]]cyclopropane, 1,1-bis[2-[(4S)-phenyl-5,5-di(2-methoxybenzyl)oxazoline]]cyclopropane, 1,1-bis[2-[(4S)-phenyl-5,5-di(3-methoxybenzyl)oxazoline]]cyclopropane, 1,1-bis[2-[(4S)-phenyl-5,5-di(4-methoxybenzyl)oxazoline]]cyclopropane, 1,1-bis[2-[(4S)-phenyl-5,5-di(1-naphthylmethyl)oxazoline]]cyclopropane, 1,1-bis[2-[(4S)-phenyl-5,5-di(2-naphthylmethyl)oxazoline]]cyclopropane, 1,1-bis[2-[(4S)-phenyl-5,5-diphenyloxazoline]]cyclopropane, 1,1-bis[2-[(4S)-phenyl-5,5-di(3-methylphenyl)oxazoline]]cyclopropane, 1,1-bis[2-[(4S)-phenyl-5,5-di(4-methylphenyl)oxazoline]]cyclopropane, 1,1-bis[2-[(4S)-phenyl-5,5-di(2-methoxyphenyl)oxazoline]]cyclopropane, 1,1-bis[2-[(4S)-phenyl-5,5-di(3-methoxyphenyl)oxazoline]]cyclopropane, 1,1-bis[2-[(4S)-phenyl-5,5-di(4-methoxyphenyl)oxazoline]]cyclopropane, 1,1-bis[2-[spiro[(4S)-phenyloxazoline-5,1'-cyclopropane]]]cyclopropane, 1,1-bis[2-[spiro[(4S)-phenyloxazoline-5,1'-cyclopentane]]]cyclopropane, 1,1-bis[2-[spiro[(4S)-phenyloxazoline-5,1'-cycloheptane]]]cyclopropane, 1,1-bis[2-[(4S)-(2-methoxyphenyl)oxazoline]]cyclopropane, 1,1-bis[2-[(4S)-(2-methoxyphenyl)-5,5-dimethyloxazoline]]cyclopropane, 1,1-bis[2-[(4S)-(2-methoxyphenyl)-5,5-diethyloxazoline]]cyclopropane, 1,1-bis[2-[(4S)-(2-methoxyphenyl)-5,5-di-n-propyloxazoline]]cyclopropane, 1,1-bis[2-[(4S)-(2-methoxyphenyl)-5,5-di-n-butyloxazoline]]cyclopropane, 1,1-bis[2-[(4S)-(2-methoxyphenyl)-5,5-diisobutyloxazoline]]cyclopropane, 1,1-bis[2-[(4S)-(2-methoxyphenyl)-5,5-di-n-pentyloxazoline]]cyclopropane, 1,1-bis[2-[(4S)-(2-methoxyphenyl)-5,5-di-n-hexyloxazoline]]cyclopropane, 1,1-bis[2-[(4S)-(2-methoxyphenyl)-5,5-dibenzyloxazoline]]cyclopropane, 1,1-bis[2-[(4S)-(2-methoxyphenyl)-5,5-di(2-methylbenzyl)oxazoline]]cyclopropane, 1,1-bis[2-

[(4S)-(2-methoxyphenyl)-5,5-di(3-methylbenzyl)oxazoline]]cyclopropane, 1,1-bis[2-[(4S)-(2-methoxyphenyl)-5,5-di(4-methylbenzyl)oxazoline]]cyclopropane, 1,1-bis[2-[(4S)-(2-methoxyphenyl)-5,5-di(2-methoxybenzyl)oxazoline]]cyclopropane, 1,1-bis[2-[(4S)-(2-methoxyphenyl)-5,5-di(3-methoxybenzyl)oxazoline]]cyclopropane, 1,1-bis[2-[(4S)-(2-methoxyphenyl)-5,5-di(4-methoxybenzyl)oxazoline]]cyclopropane,
1,1-bis[2-[(4S)-(2-methoxyphenyl)-5,5-di(1-naphthylmethyl)oxazoline]]cyclopropane, 1,1-bis[2-[(4S)-(2-methoxyphenyl)-5,5-di(2-naphthylmethyl)oxazoline]]cyclopropane, 1,1-bis[2-[(4S)-(2-methoxyphenyl)-5,5-diphenyloxazoline]]cyclopropane, 1,1-bis[2-[(4S)-(2-methoxyphenyl)-5,5-di(3-methylphenyl)oxazoline]]cyclopropane, 1,1-bis[2-[(4S)-(2-methoxyphenyl)-5,5-di(4-methylphenyl)oxazoline]]cyclopropane, 1,1-bis[2-[(4S)-(2-methoxyphenyl)-5,5-di(2-methoxyphenyl)oxazoline]]cyclopropane, 1,1-bis[2-[(4S)-(2-methoxyphenyl)-5,5-di(3-methoxyphenyl)oxazoline]]cyclopropane, 1,1-bis[2-[(4S)-(2-methoxyphenyl)-5,5-di(4-methoxyphenyl)oxazoline]]cyclopropane, 1,1-bis[2-[spiro[(4S)-(2-methoxyphenyl)oxazoline-5,1'-cyclopropane]]]cyclopropane, 1,1-bis[2-[spiro[(4S)-(2-methoxyphenyl)oxazoline-5,1'-cyclopentane]]]cyclopropane, 1,1-bis[2-[spiro[(4S)-(2-methoxyphenyl)oxazoline-5,1'-cycloheptane]]]cyclopropane; these compounds in which cross-linked ring structure at the 2-positon of the oxazoline ring is replaced with a cyclobutane, cyclopentane or cyclohexane ring; and these compounds of which the configuration (4S) at the 4-positon of the oxazoline ring is changed to (4R) such as 1,1-bis[2-[(4R)-methyloxazoline]]cyclopropane.

The optically active bisoxazoline compound (1) can be produced according to a known method such as a reaction of a 2,2-methylenebisoxazoline compound, which is obtained by the reaction of the corresponding optically active aminoalcohol and a malonimidate, and 1,2-dibromoethane in the presence of a strong base (e.g. Journal of Organic Chemistry, 65, 5875 (2000)).

The novel asymmetric copper complex can be obtained by bringing the optically active bisoxazoline compound (1) into contact with the copper compound usually in the presence of a solvent.

The optically active bisoxazoline compound (1) has two asymmetric carbon atoms as described above and at least two kinds of the optically active isomers in which these are the asymmetric centers exist and any of them may be used.

Examples of the copper compounds include a monovalent and divalent copper compound. Specific examples thereof include copper(I) trifluoromethanesulfonate, copper(II) trifluoromethanesulfonate, copper(I) acetate, copper(II) acetate, copper(I) bromide, copper(II) bromide, copper(I) chloride, copper(II) chloride and copper(I) tetrakisacetonitrile. Among them, copper(I) trifluoromethanesulfonate is preferable. These copper compounds may be used alone, or two or more thereof may be mixed to use.

The amount of the optically active bisoxazoline compound (1) to be used is usually 0.8 to 5 moles, preferably about 0.9 to 2 moles relative to 1 mole of the copper compound.

Examples of the solvents include halogenated hydrocarbon solvents such as dichloromethane, dichloroethane, chloroform and carbon tetrachloride; and aromatic hydrocarbon solvents such as benzene, toluene and xylene. When the prochiral olefin represented by the formula (2) (hereinafter, simply referred to as the olefin (2)), which is a raw material in cyclopropanation of the next step, is a liquid, the olefin (2) may be used as the solvent. The amount of the solvent to be used is usually about 10 to 500 parts by weight relative to 1 part by weight of the copper compound.

The operation of contacting the optically active bisoxazoline compound (1) with the copper compound is usually carried out in an atmosphere of an inert gas such as argon gas and nitrogen gas. The temperature of the operation is usually about −20 to 100° C.

The asymmetric copper complex obtained may be isolated from the solution obtained in the operation to be used in the reaction of the olefin (2) and the diazoacetic acid ester represented by the formula (3) (hereinafter, simply referred to as the diazoacetic acid ester (3)), and may be used as such in the form of the solution without isolation.

Next, the process for producing the optically active cyclopropane compound represented by the formula (4) (hereinafter, simply referred to as the optically active cyclopropane compound (4)) by reacting the olefin (2) with the diazoacetic acid ester (3) in the presence of the asymmetric copper complex will be illustrated.

$R^3$, $R^4$, $R^5$ and $R^6$ of the olefin (2) will be illustrated below.

Examples of the halogen atoms represented by $R^3$, $R^4$, $R^5$ or $R^6$ include a fluorine, chlorine, bromine and iodine atom.

Examples of the substituted alkyl groups represented by $R^3$, $R^4$, $R^5$ or $R^6$ include alkyl groups substituted with at least one group selected from a halogen atom, an alkoxy group, an aralkyloxy group, an acyloxy group, an alkoxycarbonyloxy group and an aryloxycarbonyloxy group.

Specific examples of the unsubstituted alkyl groups include C1-6 unsubstituted alkyl groups such as a methyl, ethyl, n-propyl, isopropyl, n-butyl, isobutyl, n-pentyl, and hexyl group.

Examples of the substituents of the substituted alkyl groups include a halogen, an alkoxy group, an aralkyloxy group, an acyloxy group, an alkoxycarbonyloxy group and an aryloxycarbonyloxy group.

Specific examples of the substituted alkyl groups include alkyl groups substituted with a halogen atom such as a chloromethyl, fluoromethyl, trifluoromethyl and chloroethyl group; alkyl groups substituted with an alkoxy group (for example, a C1-4 alkoxy group) such as a methoxymethyl, ethoxymethyl, n-propoxymethyl, isopropoxymethyl, n-butoxymethyl and tert-butoxymethyl group; alkyl groups substituted with an aralkyloxy group such as a benzyloxymethyl group; alkyl groups substituted with an acyloxy group such as an acetoxymethyl and benzoyloxymethyl group; alkyl groups substituted with an alkoxycarbonyloxy group (for example, a carbonyloxy group substituted with a C1-4 alkyl group) such as methoxycarbonyloxymethyl, ethoxycarbonyloxymethyl and tert-butoxycarbonyloxymethyl group; and alkyl groups substituted with an aryloxycarbonyloxy group such as a phenyloxycarbonyloxymethyl group.

Examples of the substituted alkenyl groups include alkenyl groups substituted with a halogen atom or an alkoxycarbonyl group. Examples of the unsubstituted alkenyl groups include C2-6 unsubstituted alkenyl groups such as a vinyl, 1-propenyl, 2-propenyl, 2-methyl-1-propenyl, 1-butenyl, 2-butenyl and 3-butenyl group. Examples of the alkenyl groups substituted with the halogen atom or the alkoxycarbonyl group include a 1-chloro-2-propenyl and 2-methoxycarbonyl-1-propenyl group.

Examples of the unsubstituted aryl groups include a phenyl, 1-naphthyl and 2-naphthyl group. Examples of the substituted aryl groups include aryl groups substituted with at least one substituent selected from an alkyl group, an alkoxy group and a halogen atom. Specific examples thereof include aryl groups substituted with the alkyl group (for example, a methyl group) such as a 2-methylphenyl, 4-methylphenyl and 3-methyphenyl group, aryl groups substituted with the alkoxy group (for example, a methoxy group) and aryl groups substituted with the halogen atom such as a chlorine, fluorine and bromine atom.

Examples of the substituted or unsubstituted aralkyl groups include the same as in $R^1$ or $R^2$.

Examples of the substituted or unsubstituted alkyl groups of the substituted or unsubstituted alkoxycarbonyl groups include the above-mentioned substituted or unsubstituted alkyl groups. Specific examples of the substituted or unsubstituted alkoxycarbonyl groups include a methoxycarbonyl, ethoxycarbonyl, n-propyloxycarbonyl, isopropyloxycarbonyl, n-butyloxycarbonyl, isobutyloxycarbonyl and n-pentyloxycarbonyl group.

Examples of the olefin (2) include propene, 1-fluoro-1-chloroethylene, 1-butene, 1-pentene, 1-hexene, 1-octene, 4-chloro-1-butene, 2-pentene, 2-heptene, 2-methyl-2-butene, 2,5-dimethyl-2,4-hexadiene, 2-chloro-5-methyl-2,4-hexadiene, 2-fluoro-5-methyl-2,4-hexadiene, 1,1,1-trifluoro-5-methyl-2,4-hexadiene, 2-methoxycarbonyl-5-methyl-2,4-hexadiene, 1,1-difluoro-4-methyl-1,3-pentadiene, 1,1-dichloro-4-methyl-1,3-pentadiene, 1,1-dibromo-4-methyl-1,3-pentadiene, 1-chloro-1-fluoro-4-methyl-1,3-pentadiene, 1-fluoro-1-bromo-4-methyl-1,3-pentadiene, 2-methyl-2,4-hexadiene, 1-fluro-1,1-dichloro-4-methyl-2-pentene, 1,1,1-trichloro-4-methyl-3-pentene, 1,1,1-tribromo-4-methyl-3-pentene, 2,3-dimethyl-2-pentene, 2-methyl-3-phenyl-2-butene, 2-bromo-2,5-dimethyl-4-hexene, 2-chloro-2,5-dimethyl-4-hexene, 1-chloro-2,5-dimethyl-2,4-hexadiene, isobutenylmethyl methyl ether, isobutenylmethyl tert-butyl ether, isobutenylmethyl benzyl ether, 3-methyl-2-butenyl acetate, 3-methyl-2-butenyl benzoate, 3-methyl-2-butenyl methyl carbonate, 3-methyl-2-butenyl tert-butyl carbonate and 3-methyl-2-butenyl phenyl carbonate.

In the formula of the diazoacetic acid ester (3), $R^7$ represents an alkyl group having 1 to 6 carbon atoms and examples thereof include the same as those exemplified above. Examples of the diazoacetic acid ester (3) include ethyl diazoacetate, n-propyl diazoacetate, isopropyl diazoacetate, n-butyl diazoacetate, isobutyl diazoacetate, tert-butyl diazoacetate, pentyl diazoacetate, and hexyl diazoacetate. A method for producing the diazoacetic acid ester (3) is not particularly limited and for example, those synthesized by a known method such as Organic Synthesis Collective Volume 3, p. 392 may be used.

The amount of the asymmetric copper complex to be used is usually 0.00001 to 0.5 mole, preferably about 0.0001 to 0.05 mole in terms of the copper metal relative to 1 mole of the diazoacetic acid ester (3).

The amount of the olefin (2) to be used is usually 1 mole or more, preferably 1.2 moles or more relative to 1 mole of the diazoacetic acid ester (3). There is no specific upper limit and, when the olefin (3) is a liquid, large excess thereof may be used also to serve as the solvent.

The reaction of the olefin (2) and the diazoacetic acid ester (3) is usually carried out by bringing three components, the asymmetric copper complex, the olefin (2) and the diazoacetic acid ester (3), into contact with one another and mixing them, and the mixing order is not particularly limited. Usually, the diazoacetic acid ester (3) is added to a mixture of the asymmetric copper complex and the olefin (2).

The reaction is usually carried out in the presence of a solvent, and examples of the solvents include halogenated hydrocarbon solvents such as dichloromethane, dichloromethane, chloroform and carbon tetrachloride; aliphatic hydrocarbon solvents such as hexane, heptane and cyclohexane; aromatic hydrocarbon solvents such as benzene, toluene and xylene; and ester solvents such as ethyl acetate. They can be used alone or in the form of a mixed solvent. Although the amount of the solvent to be used is not particularly limited, in view of the volume efficiency and the properties of the reaction mixture, the amount thereof is usually about 2 to 30 parts by weight, preferably about 5 to 20 parts by weight relative to 1 part by weight of the diazoacetic acid ester (3). The solvent may be mixed previously with the olefin (2), the diazoacetic acid ester (3) and/or the asymmetric copper complex. As described above, when the olefin (2) is a liquid, the olefin (2) may also be used as the solvent.

The reaction of the olefin (2) and the diazoacetic acid ester (3) is usually carried out in an atmosphere of an inert gas such as argon gas or nitrogen gas. Since water adversely affects the reaction, the reaction is preferably carried out with suppressing the amount of water present in the reaction system by, for example, carrying out the reaction in the presence of a dehydrating agent in the reaction system, or using the olefin (2) or the solvent previously subjected to dehydration treatment.

The reaction temperature is usually about −50 to 150° C., preferably about −20 to 80° C.

After completion of the reaction, the optically active cyclopropane compound (4) can be isolated by, for example, concentrating the reaction mixture. The optically active cyclopropane compound (4) isolated may be further purified, if necessary, by a conventional purification means such as distillation and column chromatography.

Examples of the optically active cyclopropane compound (4) include optically active methyl 2-methylcyclopropanecarboxylate, optically active methyl 2,2-dimethyl-3-(2-methyl-1-propenyl)cyclopropanecarboxylate, optically active methyl 2,2-dimethyl-3-(2,2-dichloro-1-ethenyl)cyclopropanecarboxylate, optically active methyl 2,2-dimethyl-3-(2,2,2-trichloroethyl)cyclopropanecarboxylate, optically active methyl 2,2-dimethyl-3-(2,2,2-tribromoethyl)cyclopropanecarboxylate, optically active methyl 2,2-dimethyl-3-(2,2-dibromo-1-ethenyl)cyclopropanecarboxylate, optically active methyl 2,2-dimethyl-3-(2,2-difluoro-1-ethenyl)cyclopropanecarboxylate, optically active methyl 2,2-dimethyl-3-(2-fluoro-2-chloro-1-ethenyl)cyclopropanecarboxylate, optically active methyl 2,2-dimethyl-3-(2-fluoro-2-bromo-1-ethenyl)cyclopropanecarboxylate, optically active methyl 2,2-dimethyl-3-(2-fluoro-1-propenyl)cyclopropanecarboxylate, optically active methyl 2,2-dimethyl-3-(2-chloro-1-propenyl)cyclopropanecarboxylate, optically active methyl 2,2-dimethyl-3-(2-chloro-2-trifluoromethylethenyl) cyclopropanecarboxylate, optically active methyl 2,2-dimethyl-3-(2-methoxycarbonyl-1-propenyl) cyclopropanecarboxylate, optically active methyl 2,2-dimethyl-3-(2-chloro-2-methylpropyl) cyclopropanecarboxylate, optically active methyl 2,2-dimethyl-3-(2-bromo-2-methylpropyl) cyclopropanecarboxylate, optically active methyl 2,2-dimethyl-3-(1-propenyl)cyclopropanecarboxylate, optically active methyl 3,3-dimethyl-2-(methoxymethyl)cyclopropanecarboxylate, optically active methyl 3,3-dimethyl-2-(tert-butoxymethyl)cyclopropanecarboxylate, optically active methyl 3,3-dimethyl-2-(benzyloxymethyl)cyclopropanecarboxylate, optically active methyl 3,3-dimethyl-2-(acetoxymethyl)cyclopropanecarboxylate, optically active methyl 3,3-dimethyl-2-(benzoyloxymethyl)cyclopropanecarboxylate, optically active methyl 3,3-dimethyl-2-(methoxycarbonyloxymethyl)cyclopropanecarboxylate, optically active methyl 3,3-dimethyl-2-(tert-butoxycarbonyloxymethyl) cyclopropanecarboxylate and optically active methyl 3,3-dimethyl-2-(phenoxycarbonyloxymethyl)cyclopropanecarboxylate; and compounds wherein the above methyl ester moieties are replaced with ethyl, n-propyl, isopropyl, isobutyl or tert-butyl ester moieties.

The optically active cyclopropane compound (4) can be converted into an optically active cyclopropanecarboxylic acid compound in which $R^7$ is a hydrogen atom by hydrolysis according to a known hydrolysis method.

EXAMPLES

The present invention will be further illustrated in more detail by Examples. The present invention is not limited to these Examples.

In each Examples and Comparative Examples, the yield was calculated by the gas chromatography internal standard method, and the trans-isomer/cis-isomer ratio was calculated based on the area ratio of the gas chromatography. The optically purity was calculated based on the area ratio of the liquid chromatography.

Example 1

In a 50 mL Schlenk tube purged with nitrogen, 12.9 mg (0.050 mmol) of copper(I) trifluoromethanesulfonate toluene complex and 5 mL of dichloroethane were mixed and 16.1 mg (0.055 mmol) of 1,1-bis[2-[(4S)-(tert-butyl)-oxazoline]]cyclopropane was added into the cloudy mixture obtained and the resulting mixture was stirred at room temperature for 10 minutes to obtain the yellow homogenous solution containing the asymmetric copper complex. After that, 2.56 g (20 mmol) of 3-methyl-2-butenyl acetate was added to the solution and the inner temperature was adjusted to 0° C. 6 mL of the dichloroethane solution containing 1.14 g (10 mmol) of ethyl diazoacetate was added dropwise thereto over 2 hours and the resulting mixture was stirred at the same temperature for 30 minutes to effect reaction and the solution containing ethyl 3,3-dimethyl-2-(acetoxymethyl)cyclopropanecarboxylate was obtained.

Yield: 54% (based on ethyl diazoacetate) trans-isomer/cis-isomer ratio: 84/16

Herein, the trans-isomer means the compound having the ester group at 1-position and the acetoxymethyl group at 2-position on the opposite side with respect to the cyclopropane ring plane and the cis-isomer means the compound having the ester group at 1-position and the actoxymethyl group at 2-position on the same side (the same in the Comparative Example 1)).

Optically purity: trans-isomer 97% e.e. ((+)-isomer), cis-isomer 42% e.e. ((+)-isomer)

Comparative Example 1

According to the same manner as that described in Example 1, the solution containing ethyl 3,3-dimethyl-2-(acetoxymethyl)cyclopropanecarboxylate was obtained except that 16.2 mg (0.055 mmol) of 2,2-bis[2-[(4S)-(tert-butyl)-oxazoline]]propane was used in place of 16.1 mg (0.055 mmol) of 1,1-bis[2-[(4S)-(tert-butyl)-oxazoline]]cyclopropane.

Yield: 55% (based on ethyl diazoacetate) trans-isomer/cis-isomer ratio: 80/20 Optically purity: trans-isomer 97% e.e. ((+)-isomer), cis-isomer 67% e.e. ((+)-isomer)

Example 2

Into a 50 mL Schlenk tube purged with nitrogen, 6.47 mg (0.025 mmol) of copper(I) trifluoromethanesulfonate toluene complex, 8.00 mg (0.027 mmol) of 1,1-bis[2-[(4S)-(tert-butyl)-oxazoline]]cyclopropane and 5 mL of dichloroethane were added and the resulting mixture was stirred at room temperature for 10 minutes to obtain the solution containing the asymmetric copper complex. After that, 8.81 g (50 mmol) of 3-methyl-2-butenyl benzyl ether was added to the solution and the inner temperature was adjusted to 0°0 C. 10 mL of the dichloroethane solution containing 2.85 g (25 mmol) of ethyl diazoacetate was added dropwise thereto over 2 hours and the resulting mixture was stirred at the same temperature for 30 minutes to effect reaction and the solution containing ethyl 3,3-dimethyl-2-(benzyloxymethyl)cyclopropanecarboxylate was obtained.

Yield: 82% (based on ethyl diazoacetate) trans-isomer/cis-isomer ratio: 94/6

Herein, the trans-isomer means the compound having the ester group at 1-position and the benzyloxymethyl group at 2-position on the opposite side with respect to the cyclopropane ring plane and the cis-isomer means the compound having the ester group at 1-position and the benzyloxymethyl group at 2-position on the same side (the same in the Comparative Example 2)).

1 g of the oily matter obtained by concentrating the reaction mixture was taken and 4 mL of 2N aqueous sodium hydroxide was added thereto. The mixture was stirred at an inner temperature of 100° C. for 2 hours. Neutralization by 1N hydrochloric acid, extraction by hexane and concentration were carried out to obtain 3,3-dimethyl-2-benzyloxymethylcyclopropanecarboxylic acid.

Optically purity: trans-isomer 97% e.e. ((+)-isomer), cis-isomer 11% e.e. ((+)-isomer)

Comparative Example 2

According to the same manner as that described in Example 2, the solution containing ethyl 3,3-dimethyl-2-(benzyloxymethyl)cyclopropanecarboxylate was obtained except that 8.09 mg (0.027 mmol) of 2,2-bis[2-[(4S)-(tert-butyl)-oxazoline]]propane was used in place of 8.00 mg (0.027 mmol) of 1,1-bis[2-[(4S)-(tert-butyl)-oxazoline]]cyclopropane.

Yield: 74% (based on ethyl diazoacetate) trans-isomer/cis-isomer ratio: 89/11 Optically purity: trans-isomer 94% e.e. ((+)-isomer), cis-isomer 10% e.e. ((+)-isomer)

Example 3

Into a 50 mL Schlenk tube purged with nitrogen, 12.9 mg (0.050 mmol) of copper(I) trifluoromethanesulfonate toluene complex, 16.1 mg (0.055 mmol) of 1,1-bis[2-[(4S)-(tert-butyl)-oxazoline]]cyclopropane and 5 mL of dichloroethane were added and the resulting mixture was stirred at room temperature for 10 minutes to obtain the solution containing the asymmetric copper complex. After that, 2.88 g (20 mmol) of isobutenylmethyl methyl carbonate was added to the solution and the inner temperature was adjusted to 0° C. 6 mL of the dichloroethane solution containing 1.14 g (10 mmol) of ethyl diazoacetate was added dropwise thereto over 2 hours and the resulting mixture was stirred at the same temperature for 30 minutes to effect reaction and the solution containing ethyl 3,3-dimethyl-2-(methoxycarbonyloxymethyl)cyclopropanecarboxylate was obtained.

Yield: 68% (based on ethyl diazoacetate) trans-isomer/cis-isomer ratio: 90/10

Herein, the trans-isomer means the compound having the ester group at 1-position and the methoxycarbonyloxymethyl group at 2-position on the opposite side with respect to the cyclopropane ring plane and the cis-isomer means the compound having the ester group at 1-position and the methoxycarbonyloxymethyl group at 2-position on the same side (the same in the Comparative Example 3)).

Optically purity: trans-isomer 96% e.e. ((+)-isomer), cis-isomer 0% e.e. ((+)-isomer)

Comparative Example 3

According to the same manner as that described in Example 3, the solution containing ethyl 3,3-dimethyl-2-(methoxycarbonyloxymethyl)cyclopropanecarboxylate was obtained except that 16.2 mg (0.055 mmol) of 2,2-bis[2-[(4S)-(tert-butyl)-oxazoline]]propane was used in place of 16.1 mg (0.055 mmol) of 1,1-bis[2-[(4S)-(tert-butyl)-oxazoline]]cyclopropane.

Yield: 66% (based on ethyl diazoacetate) trans-isomer/cis-isomer ratio: 84/16 Optically purity: trans-isomer 93% e.e. ((+)-isomer), cis-isomer 6% e.e. ((+)-isomer)

INDUSTRIAL APPLICABILITY

According to the process of the present invention, it is possible to produce an optically active transcyclopropane compound efficiently from a diazoacetic acid lower alkyl ester which is industrially advantageous and a prochiral olefin by using the novel asymmetric copper complex prepared from the optically active cycloalkylidenebisoxazoline compound and the copper compound.

In the process for producing (+)-trans-2,2-dimethyl-3-(2-methyl-1-propenyl)cyclopropanecarboxylate and (+)-trans-3,3-dimethyl-2-(benzyloxymethyl)cyclopropanecarboxylate, it is superior to (+)-trans selectivity and it is industrially advantageous.

The invention claimed is:

1. A process for producing an optically active cyclopropane compound represented by the formula (4):

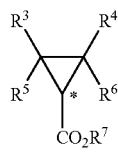

(4)

wherein $R^3$, $R^4$, $R^5$ and $R^6$ are the same or different, and represent a hydrogen atom, a halogen atom, a substituted or unsubstituted alkyl group,
a substituted or unsubstituted alkenyl group, a substituted or unsubstituted aryl group,
a substituted or unsubstituted aralkyl group or
a substituted or unsubstituted alkoxycarbonyl group;
provided that, when $R^3$ and $R^5$ are the same, $R^4$ and $R^6$ are different from each other; and
$R^7$ represents an alkyl group having 1 to 6 carbon atoms, which comprises reacting a prochiral olefin represented by the formula (2):

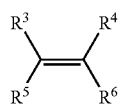

(2)

wherein $R^3$, $R^4$, $R^5$, and $R^6$ are as described above, with a diazoacetic acid ester represented by the formula (3):

$$N_2CHCO_2R^7 \qquad (3)$$

wherein $R^7$ is as defined above,
in the presence of an asymmetric copper complex prepared from an optically active cycloalkylidenebisoxazoline compound represented by the formula (1):

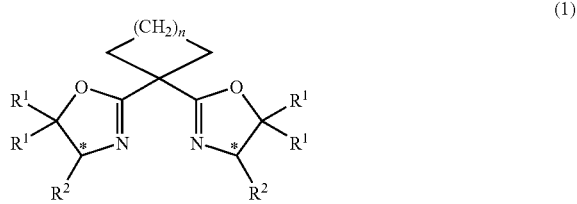

(1)

wherein $R^1$ represents a hydrogen atom, a C1-6 alkyl group, a substituted or unsubstituted aralkyl group or a substituted or unsubstituted phenyl group,
$R^2$ represents a C1-6 alkyl group, a substituted or unsubstituted aralkyl group or a substituted or unsubstituted phenyl group, and n represents an integer of 0 to 3;
provided that, when $R^1$ represents a C1-6 alkyl group, two $R^1$s which are bonded to the same carbon atom may be bonded together with the carbon atom to which they are bonded to form a ring; and * represents an asymmetric carbon atom; and a copper compound.

2. The process according to claim 1, wherein the copper complex obtained by bringing the optically active cycloalkylidenebisoxazoline compound represented by the formula (1) into contact with the copper compound in the presence of a solvent is used.

3. The process according to claim 1, wherein n is 0.

4. The process according to claim 1, wherein $R^2$ is a tert-butyl group.

5. The process according to claim 1, wherein the optically active cycloalkylidenebisoxazoline compound represented by the formula (1) is optically active 1,1-bis[2-(4-tert-butyloxazoline)]cyclopropane.

6. The process according to claim 1, wherein the copper compound is a monovalent or divalent copper trifluoromethanesulfonate.

7. The process according to claim 1, wherein $R^1$ represents a hydrogen atom, a C1-6 alkyl group,
a C7-15 aralkyl group which may be substituted with at least one substituent selected from a C1-6 alkyl group and a C1-6 alkoxy group, or
a phenyl group which may be substituted with at least one substituent selected from a C1-6 alkyl group and a C1-6 alkoxy group, and
$R^2$ represents a C1-6 alkyl group,
a C7-15 aralkyl group which may be substituted with at least one substituent selected from a C1-6 alkyl group and a C1-6 alkoxy group, or
a phenyl group which may be substituted with at least one substituent selected from a C1-6 alkyl group and a C1-6 alkoxy group.

8. The process according to claim 1, wherein the optically active bisoxazoline compound is 1,1-bis[2-(4S)-(tert-butyl)-oxazoline]]cyclopropane.

* * * * *